United States Patent [19]

Clements-Jewery et al.

[11] Patent Number: 4,794,122

[45] Date of Patent: Dec. 27, 1988

[54] NOVEL BENZIMIDAZOLYL-THIOMETHYL-BENZOTHIAZOLES

[75] Inventors: Stephen Clements-Jewery, Ashton Keynes Near Swindon; Peter D. Kennewell, Swindon; Robert Westwood, Kingston Bagpulze, all of Great Britain

[73] Assignee: Roussel Uclaf, Paris, France

[21] Appl. No.: 57,758

[22] Filed: Jun. 3, 1987

[30] Foreign Application Priority Data

Jun. 4, 1986 [GB] United Kingdom ............... 8613592

[51] Int. Cl.$^4$ .................. A61K 31/425; C07D 417/12
[52] U.S. Cl. ..................................... 514/367; 548/159
[58] Field of Search ......................... 548/159; 514/367

[56] References Cited

U.S. PATENT DOCUMENTS 2,614,957 10/1952 Somerville et al. .................. 514/367
3,558,775 1/1971 Fournier et al. ..................... 514/395
4,600,722 6/1986 Uhlendorf et al. ................. 514/367

FOREIGN PATENT DOCUMENTS 4806 9/1965 France.

Primary Examiner—Mary E. Ceperley
Attorney, Agent, or Firm—Bierman & Muserlian

[57] ABSTRACT

A compound selected from the group consisting of a compound of the formula

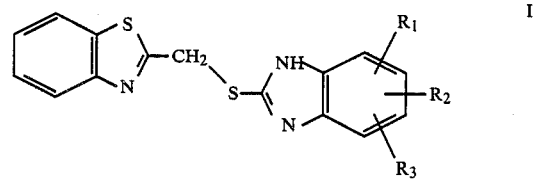

wherein $R_1$, $R_2$ and $R_3$ are individually selected from the group consisting of hydrogen, halogen and alkyl and alkoxy of 1 to 6 carbon atoms and their non-toxic, pharmaceutically acceptable acid addition salts having anti-allergic and anti-inflammatory properties.

18 Claims, No Drawings

NOVEL BENZIMIDAZOLYL-THIOMETHYL-BENZOTHIAZOLES

OBJECTS OF THE INVENTION

It is an object of the invention to provide the novel compounds of Formula I and their non-toxic, pharmaceutically acceptable acid addition salts and their preparation.

It is another object of the invention to provide novel anti-allergic and anti-inflammatory compositions and to provide a novel method of treating allergic and inflammatory conditions in warm-blooded animals.

These and other objects and advantages of the invention will become obvious from the following detailed description.

THE INVENTION

The novel compounds of the invention are selected from the group consisting of a compound of the formula

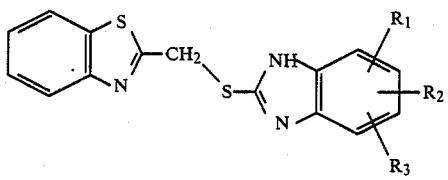

wherein $R_1$, $R_2$ and $R_3$ are individually selected from the group consisting of hydrogen, halogen and alkyl and alkoxy of 1 to 6 carbon atoms and their non-toxic, pharmaceutically acceptable acid addition salts.

Among the preferred halogens are chlorine and bromine. Examples of alkyl and alkoxy of 1 to 6 carbom atoms are methyl, ethyl, n-propyl, isopropyl, methoxy, ethoxy, n-propoxy, isopropoxy and linear and branched butyl, pentyl, hexyl, butoxy, pentyloxy and hexyloxy.

Examples of suitable acids for the non-toxic, pharmaceutically acceptable acid addition salts are inorganic acids such as hydrochloric acid, hydrobromic acid, hydroiodic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid and aspartic acid, aryl carboxylic acids such as benzoic acid, alkane sulfonic acids such as methanesulfonic acid and aryl sulfonic acids such as benzene sulfonic acid.

Among the preferred compounds of Formula I are those wherein $R_1$, $R_2$ and $R_3$ are individually hydrogen, chlorine, methyl and/or methoxy, preferably chlorine or hydrogen and their non-toxic, pharmaceutically acceptable acid addition salts. Specific preferred compounds are 2-(5,6-dichloro-1H-benzimidazol-2-yl-thiomethyl)-benzothiazole, 2-(5-chloro-1H-benzimidazol-2-yl-thiomethyl)-benzothiazole and 2-(1H-benzimidazol-2-yl-thiomethyl)-benzothiazole and their non-toxic, pharmaceutically acceptable acid addition salts.

The novel process of the invention for the preparation of the compounds of Formula I comprises reacting a salt of a compound of the formula

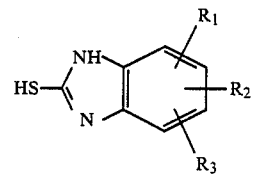

wherein $R_1$, $R_2$ and $R_3$ have the above definition with a compound of the formula

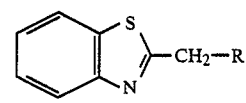

wherein R is a halogen to obtain the corresponding compound of Formula I which may be optionally salified with an acid to form the acid addition salt.

Among the preferred halogens for R are chlorine, bromine, iodine.

The reaction is preferably effected in an organic solvent such as ether, tetrahydrofuran or dimethylformamide and the salt of the compound of Formula II may be formed by reacting the compound of Formula II with an anion forming reagent such as an alkali metal hydride like sodium hydride.

The acid addition salts of Formula I may be prepared by reacting the compound of Formula I with an approximately stoichiometric amount of the acid with or without previous isolation of the compound of Formula I.

The novel anti-inflammatory and anti-allergic compositions of the invention are comprised of an anti-inflammatory and anti-allergically effective amount of at least one compound of Formula I and their non-toxic, pharmaceutically acceptable acid addition salts and an inert pharmaceutical carrier or excipient. The compositions may be in the form of tablets, dragees, capsules, powders, suppositories, aerosols, creams, ointments and injectable solutions or suspensions.

Examples of suitable excipients are talc, gum arabic, lactose, starch, magnesium stearate, cocoa butter, aqueous and non-aqueous vehicles, animal or vegetable fats, paraffin derivatives, glycols, various wetting agents, dispersants and emulsifiers and preservatives.

The compositions have a remarkable activity towards inhibition of 5-lipoxygenase and binding of leukotriene $D_4$ to its receptors making them useful as anti-allergic and anti-inflammatory compositions. They are useful in the treatment of allergic asthmatic conditions, bronchitis of allergic origin and inflammatory conditions.

The novel method of the invention for treating allergic and inflammatory conditions in warm-blooded animals, including humans, comprising administering to warm-blooded animals an anti-allergically and anti-inflammatorily effective amount of at least one compound of Formula I and their non-toxic, pharmaceutically acceptable acid addition salts. The compounds may be administered orally, rectally, topically or parenterally and the usual daily dose is 0.0015 to 2.75 mg/kg depending on the compound used, the condition treated and the method of administration.

In the following examples there are described several preferred embodiments to illustrate the invention. However, it should be understood that the invention is not intended to be limited to the specific embodiments.

EXAMPLE 1

2-(1H-benzimidazol-2-yl-thiomethyl)-benzothiazole 1.5 g (50 mmol-80%) of sodium hydride were added under nitrogen to a stirred solution of 7.6 g (50 mmol) of 2-benzimidazolethiol in 76 ml of dimethylformamide and after one hour, 7.2 g (40 mmol) of 2-chloromethyl-benzothiazole were added with ice cooling. The mixture stood at room temperature for 2 hours and the solution was concentrated under reduced pressure in a nitrogen stream. The residue was dissolved in ethyl acetate and the solution was washed with ice cold 2N sodium hydroxide solution and aqueous saturated sodium chloride solution, was dried over magnesium sulfate and evaporated to dryness under reduced pressure to obtain 6.91 g (58% yield) of 2-(1H-benzimidazol-2-yl-thiomethyl)-benzothiazole in the form of pale yellow crystals after crystallization from dichloromethane melting at 159°–162° C.

Analysis: $C_{15}H_{11}N_3S_2$: Calculated: % C 60.58; % H 3.73; % N 14.13. Found: 60.37; 3.73; 14.11.

EXAMPLE 2

Using the procedure of Example 1, there was obtained a 33% yield of 2-(5-chloro-1H-benzimidazol-2-yl-thiomethyl)benzothiazole melting at 176°–180° C.

Analysis: $C_{15}H_{10}ClN_3S_2$: Calculated: % C 54.29; % H 3.04; % N 12.66. Found: 54.03; 3.12; 12.54.

EXAMPLE 3

Using the procedure of Example 1, there was obtained a 30% yield of 2-(5,6-dichloro-1H-benzimidazol-2-yl-thiomethyl)benzothiazole melting at 209°–210° C. (decomposition).

Analysis: $C_{15}H_9Cl_2N_3S_2$: Calculated: % C 49.19; % H 2.48; % N 11.47. Found: 49.07; 2.60; 11.38.

EXAMPLE 4

Tablets were prepared containing 10 mg of the product of Example 2 or 3 and sufficient excipient of talc, starch, lactose and magnesium stearate for a final tablet weight of 100 mg.

EXAMPLE 5

A dosed aerosol was prepared delivering 1 mg of the compound of Example 3, 0.15 mg of emulsifier and 50 mg of propellant per dose.

PHARMACOLOGICAL DATA

Inhibition of $Ca^{++}$ ionophore (A23187)-induced release of 5-lipoxygenase products (leukotriene $B_4$ and 5-HETE) from [$^{14}C$]-arachidonic acid prelabelled rat peritoneal neutrophils was determined by a modification of the method of Ahnfelt-Ronne et al [Biochemical Pharmacology, Vol. 31, (1982), No. 16, p. 2619–2624]. The micro molecular concentration of the compounds causing a 50% inhibition of the control response, determined graphically from dose response curves for 5-lipoxygenase, was 3.5, 0.59 and 0.23 for the compounds of Examples 1, 2 and 3, respectively.

Various modifications of the compounds and method of the invention may be made without departing from the spirit or scope thereof and it should be understood that the invention is intended to be limited only as defined in the appended claims.

What is claimed is:

1. A compound selected from the group consisting of a compound of the formula

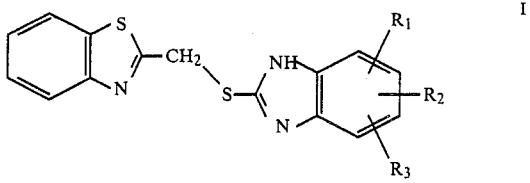

wherein $R_1$, $R_2$ and $R_3$ are individually selected from the group consisting of hydrogen, halogen and alkyl and alkoxy of 1 to 6 carbon atoms and their non-toxic, pharmaceutically acceptable acid addition salts.

2. A compound of claim 1 wherein $R_1$, $R_2$ and $R_3$ are individually selected from the group consisting of hydrogen, chlorine, methyl and methoxy.

3. A compound of claim 1 wherein $R_1$, $R_2$ and $R_3$ are individually selected from the group consisting of hydrogen and chlorine.

4. A compound of claim 1 selected from the group consisting of 2-(5,6-dichloro-1H-benzimidazol-2-yl-thiomethyl)benzothiazole and its non-toxic, pharmaceutically acceptable acid addition salts.

5. A compound of claim 1 selected from the group consisting of 2-(5-chloro-1H-benzimidazol-2-yl-thiomethyl)benzothiazole and its non-toxic, pharmaceutically acceptable acid addition salts.

6. A compound of claim 1 selected from the group consisting of 2-(1H-benzimidazol-2-yl-thiomethyl)-benzothiazole and its non-toxic, pharmaceutically acceptable acid addition salts.

7. An anti-inflammatory and anti-allergic composition comprising an anti-inflammatorily and anti-allergically effective amount of at least one compound of claim 1 and an inert pharmaceutical carrier.

8. The composition of claim 7 wherein $R_1$, $R_2$ and $R_3$ are individually selected from the group consisting of hydrogen, chlorine, methyl and methoxy.

9. The composition of claim 7 wherein $R_1$, $R_2$ and $R_3$ are individually selected from the group consisting of hydrogen and chlorine.

10. The composition of claim 7 wherein the active compound is selected from the group consisting of 2-(5,6-dichloro-1H-benzimidazol-2-yl-thiomethyl)-benzothiazole and its non-toxic, pharmaceutically acceptable acid addition salts.

11. The composition of claim 7 wherein the active compound is selected from the group consisting of 2-(5-chloro-1H-benzimidazol-2-yl-thiomethyl)-benzothiazole and its non-toxic, pharmaceutically acceptable acid addition salts.

12. The composition of claim 7 wherein the active compound is selected from the group consisting of 2-(1H-benzimidazol-2-yl-thiomethyl)-benzothiazole and its non-toxic, pharmaceutically acceptable acid addition salts.

13. A method of treating allergic and inflammatory conditions in warm-blooded animals comprising administering to warm-blooded animals an anti-allergically and anti-inflammatorily effective amount of at least one compound of claim 1.

14. The method of claim 13 wherein $R_1$, $R_2$ and $R_3$ are individually selected from the group consisting of hydrogen, chlorine, methyl and methoxy.

15. The method of claim 13 wherein $R_1$, $R_2$ and $R_3$ are individually selected from the group consisting of hydrogen and chlorine.

16. The method of claim 13 wherein the active compound is selected from the group consisting of 2-(5,6-dichloro-1H-benzimidazol-2-yl-thiomethyl)-benzothiazole and its non-toxic, pharmaceutically acceptable acid addition salts.

17. The method of claim 13 wherein the active compound is selected from the group consisting of 2-(5-chloro-1H-benzimidazol-2-yl-thiomethyl)-benzothiazole and its non-toxic, pharmaceutically acceptable acid addition salts.

18. The method of claim 13 wherein the active compound is selected from the group consisting of 2-(1H-benzimidazol-2-yl-thiomethyl)-benzothiazole and its non-toxic, pharmaceutically acceptable acid addition salts.

* * * * *